United States Patent [19]
Linde et al.

[11] Patent Number: 4,516,252
[45] Date of Patent: May 7, 1985

[54] DEVICE FOR IMAGING LAYERS OF A BODY

[75] Inventors: Rolf Linde, Haseldorf; Erhard Klotz, Halstenbek, both of Fed. Rep. of Germany

[73] Assignee: U.S. Philips Corporation, New York, N.Y.

[21] Appl. No.: 400,837

[22] Filed: Jul. 22, 1982

[30] Foreign Application Priority Data

Aug. 28, 1981 [DE] Fed. Rep. of Germany ....... 3134076

[51] Int. Cl.³ .......................... A61B 6/00; G01T 1/29; G03B 41/16
[52] U.S. Cl. ............................................ 378/23; 378/2
[58] Field of Search ...................... 378/2, 23

[56] References Cited

U.S. PATENT DOCUMENTS 2,207,867 7/1940 Loebell ................................. 378/23
3,873,834 3/1975 Dammann ........................... 378/23

FOREIGN PATENT DOCUMENTS 2746035 4/1979 Fed. Rep. of Germany.
3037621 5/1982 Fed. Rep. of Germany.

OTHER PUBLICATIONS

Dummling, K., "Ein neus Verfahren zum Mehrfachschichten mit Hilfe von Fernsehbidspeichern", Der Radiologe, vol. 9, No. 2, pp. 37–40 (Feb. 1969).
Haendle, V. J., et al., "Das elektronische Schichtbild.", Rontgenpraxis, vol. 34, pp. 253–257 (1981).

Primary Examiner—Alfred E. Smith
Assistant Examiner—T. N. Grigsby
Attorney, Agent, or Firm—Marc D. Schechter

[57] ABSTRACT

In a short-time tomosynthesis apparatus for imaging layers of a body to be examined, the body is irradiated by radiation beams from a large number of different directions in order to form perspective images. The radiation beams are detected by a detector which is arranged underneath the body. The perspective images appearing on the exit of the detector will overlap when the radiation beams have a comparatively large angle of aperture. For separating the perspective images, an image separating system is provided at the exit of the detector. The image separating system may comprise a fiber-optical system or an electron-optical deflection unit.

15 Claims, 7 Drawing Figures

U.S. Patent  May 7, 1985  4,516,252
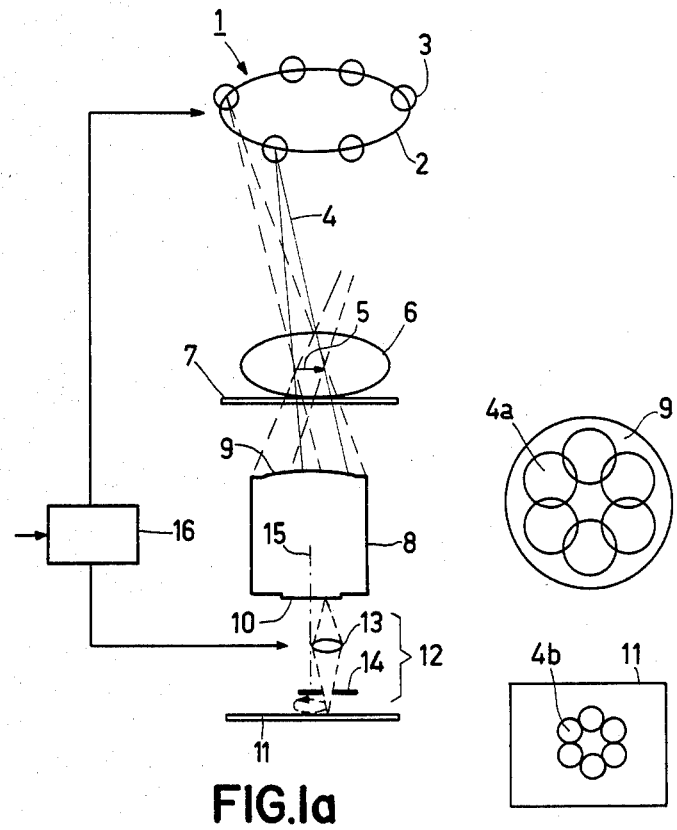
FIG.1b
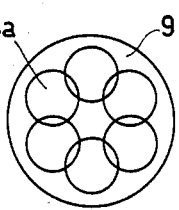
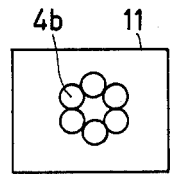
FIG.1c
FIG.1a
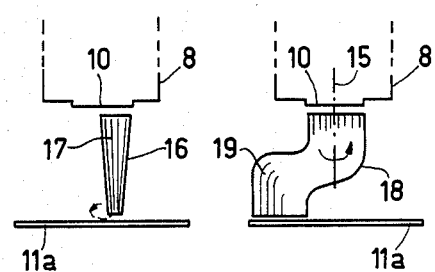
FIG.2a  FIG.2b  FIG.2c
FIG.3

DEVICE FOR IMAGING LAYERS OF A BODY

BACKGROUND OF THE INVENTION

The invention relates to a device for imaging layers of a body. The device comprises a plurality of radiation sources which are situated at radiation source positions in a plane, on one side of the body. A radiation detector is situated at the opposite side of the body in order to form perspective images. A reconstruction device superimposes the perspective images in order to form layer images.

A device of this kind is known from an article entitled "Das elektronische Schichtbild" (The electronic layer image) in *Rontgenpraxis, Volume* 34 (1981), pages 253–257. The device described therein comprises a plurality of X-ray tubes which are arranged in one plane and which can be briefly activated in succession. The radiation beams of the tubes successively irradiate an object to be examined from different perspectives. The separate projections are generated quickly in succession and are superposed in an X-ray image intensifier tube detector by magnetic deflection, so that a layer image of the irradiated object is formed on the exit screen of the X-ray image intensifier tube. Such a device forms a layer image of a body per radiation source cycle. The separate perspective images are not stored in this device.

If several layer images were to be reconstructed from a single set of projection images by means of the known device, storage of the perspective images formed during a source cycle would be necessary. In order to reduce artefacts in the reconstructed layer images, the perspective images used for reconstructing of the layer images may not overlap. This can be achieved in the known device by choosing the angles of aperture of the radiation beams to be so small that the perspective images appearing on the exit screen of the X-ray image intensifier are each situated in separate zones. It is a drawback, however, that only a comparatively small object zone can thus be irradiated.

SUMMARY OF THE INVENTION

It is the object of the invention to provide a device for imaging layers of a body, which device produces layer images containing fewer artefacts in comparison with the known device while utilizing a comparatively small detector, even when large object zones are irradiated.

This object is achieved according to the invention in that at the exit of the detector there is arranged an image recording means for recording the perspective images. Between the detector and the image recording means there is arranged an image separating system for imaging the perspective images on the image recording means in nonsuperposed form.

The image separating system may be either a light-optical unit, or an electron-optical unit and it ensures that the visible perspective images which appear on the exit of the detector, for example on the exit screen of an X-ray image intensifier, and which subsequently appear successively in zones which are not separated from one another, are separated on the image recording device. As a result the layer images have an improved image quality with respect to the layer images obtained by means of the known device.

In a preferred embodiment according to the invention, the optical image separating system comprises a lens diaphragm combination, which reduces the perspective images, or a reducing image conductor unit. The optical image separating system is successively aimed directly at each perspective image appearing on the exit of the detector.

Due to the reduction of the perspective images appearing on the exit of the detector, the separation thereof can be particularly simply performed. The information content of the perspective images (and hence of the layer images), is not reduced thereby. This is because the perspective images fully represent the previously irradiated object zone, even in the reduced condition.

During the imaging of the perspective images on the image recording device, the lens-diaphragm combination or the image conductor unit is moved in synchronism with the activation of the radiation sources. The lens-diaphragm combination is, each time, aimed directly at a perspective image appearing on the exit of the detector.

Instead of only one radiation source, several radiation sources may be activated each time. For example, two radiation sources whose radiation beams do not overlap on the entrance of the detector may be activated together. In this case, a corresponding image separating system may also consist of several lens diaphragm combinations or image conductor units which circulate in synchronism with the activation of the radiation sources.

In a further embodiment according to the invention, the radiation source positions may be situated in a circle. In this case, the optical image separating system consists of at least one suitably bent bundle of image conductors. The entrance face of the bundle is situated opposite the exit face of the detector. The bundle is arranged to be rotatable about an axis which extends perpendicularly to the detector exit face and through the center thereof, so that the perspective images are imaged on the image recording means according to their original distribution.

An image separating system thus formed ensures that the perspective images arranged in a circle on the exit face of the image converter can be imaged on the image recording means not only in separated form, but also without reduction, and even in enlarged form. On the recording means, the images are again situated in a circle which, however, has a larger diameter than the former circle.

When several radiation sources whose radiation beams do not overlap on the entrance of the detector are simultaneously activated, several suitably bent image conductor bundles can be used. The bundles are again moved in synchronism with the activated radiation sources, so that the distribution of the perspective images on the image recording means corresponds to that on the exit screen of the detector.

BRIEF DESCRIPTION OF THE DRAWING

FIG. 1*a* schematically shows a device for recording perspective images, which device has an image separating system.

FIG. 1*b* schematically shows the superposed radiation beams on the entrance face of an image intensifier.

FIG. 1*c* schematically shows the separated perspective images obtained on an image recording means by means of the radiation beams.

FIGS. 2a, 2b, and 2c schematically show different embodiments of optical image separating systems.

FIG. 3 schematically shows an electron-optical deflection unit for the separation of the perspective images, and also an associated layer image reconstruction device.

DESCRIPTION OF THE PREFERRED EMBODIMENTS

The device which is shown in FIG. 1a for the recording of perspective images comprises a radiation source means (radiation source device 1). Source device 1 consists of several X-ray tubes 3 which are arranged in a circle 2. X-ray tubes 3 can be briefly activated sequentially.

The radiation beams 4 produced by the X-ray tubes 3 are directed so that they irradiate a common zone 5 of a body 6 to be examined. Body 6 is positioned on an examination table 7. Underneath the body 6 there is arranged an X-ray image intensifier 8 which serves as the detector. The radiation beams 4 are incident on the entrance face 9 of image intensifier 8.

FIG. 1b separately shows the beam cross-sections 4a of the radiation beams 4 which are sequentially incident on the entrance face 9 of the X-ray intensifier 8. Adjacent radiation beam cross-sections 4a intersect one another (that is, they are partially spacially superposed), because the angles of aperture of the radiation beams 4 are chosen to be comparatively large. The angles are large in order to irradiate an area of body zone 5 which is as large as possible.

The perspective images (optical images) produced on the exit face 10 of the X-ray image intensifier 8 by means of the radiation beams 4 have the same distribution as shown in FIG. 1b, except that they have been reduced. Adjacent perspective images are partially spacially superposed. If such perspective images were successively stored in this superposed form, for example on a photosensitive film by means of a customary image recording means, such superposition would cause additional artefacts in the layer images reconstructed from these perspective images. A suitable method for the reconstruction of layer images from perspective images is disclosed, for example, in German Offenlegungsschrift No. 2,746,035.

In order to store in separate form, the perspective images successively obtained on the exit screen 10 of the X-ray image intensifier 8, an image recording means 11 is arranged underneath the X-ray image intensifier 8. Between the image recording means 11 and the X-ray image intensifier 8 there is arranged image separating means (image separating system 12). Image separating system 12 consists of a powerful-wide-aperture lens 13 and an associated diaphragm 14 for limiting the image format and limiting scattered radiation. Lens 13 images the perspective images on the image recording means 11 in reduced form. The reduction introduced by the image separating system 12 is chosen so that the perspective images 4b are successively imaged on the image recording means 11 with no overlap (see FIG. 1c). The image recording means 11 may consist of, for example, a photosensitive film 11a (FIGS. 2a, 2b, and 2c); or a fluorescent screen 11b for real-time superposition of the perspective images in order to form layer images. The fluorescent screen 11b will be described in detail with reference to FIG. 3.

For imaging the perspective images 4b from the exit face 10 of the X-ray image intensifier 8 onto the recording means 11, the image separating system 12 (consisting of the lens 13 and the associated diaphragm 14) is rotated in synchronism with the activation of the X-ray tubes 3. Image separating system is rotated, about an axis 15 which extends perpendicular to the exit face 10 and through the center thereof, so that the lens 13 is situated directly opposite the perspective image each time obtained on the exit face 10. A control device 16 which rotates the image separating system 12 about the axis 15 in correspondence with the X-ray tube 3 activated.

When several X-ray tubes 3 are simultaneously activated, for example two oppositely situated tubes 3 whose radiation beams 4 do not overlap on the entrance face 9 of the X-ray image intensifier 8, the image separating system 12 includes a corresponding number of lens diaphragm combinations 13 and 14. By this means the time required for recording all of the perspective images for the examination of the body 6 is substantially reduced.

The radiation source device 1 may alternatively consist of a single radiation source, for example a single X-ray tube 3 which can be successively moved to the required or predetermined radiation source positions. The radiation source can then be moved along paths other than the circular path 2, for example along a straight line. The movement of the image separating system 12 should then be adapted to this movement of the radiation source. The same is applicable to the case involving two or more radiation sources whose radiation beams 4 do not overlap on the entrance face 9 of the X-ray image intensifier 8 and which are simultaneously displaced and briefly activated each time in different radiation source positions.

For the irradiating of the body 6, the radiation beams 4 must land as much as possible in the flat zone of the entrance face 9 of the X-ray image intensifier 8. This is so that distortion of the perspective images due to the curvature of the entrance face 9 is avoided. Such residual distortion can be corrected by means of further optical or electronic elements which, however, make the construction more complex.

The FIGS. 2a, 2b and 2c show further embodiments of layer-imaging devices according to the invention. For example, the optical image separating system shown in FIG. 2a consists of a reducing bundle 16 of image conductors 17. Bundle 16 is arranged to be displaceable in correspondence with the position of the perspective image on the exit face 10 of the X-ray image intensifier 8.

The image recording means 11a herein consists of a photosensitive film for the storage of the perspective images. As in the device described with reference to FIG. 1a, the entire process of recording and storage of the perspective images can be performed within milliseconds, so that moving objects can also be recorded.

After the storage of the perspective images on the film 11a, i.e. after the exposure thereof, the film is developed. The developed film 11a is subsequently irradiated by light, so that the perspective images can be superposed to form layer images, for example by means of a lens matrix in which the lens positions correspond to the positions of the X-ray tubes during the recording of the perspective images. Using a further display device 24 as shown in FIG. 3 (for example a frosted glass plate or a television camera which can be arbitrarily positioned within the superposition zone of the perspective images), different layers within the body zone, which is irradiated by all radiation beams 4 together, can be displayed by means of the one set of perspective images.

The image separating system 12 shown in FIG. 2b consists of a suitably bent bundle 18 of image conductors 19. Such an image separating system 12 is used when the radiation source positions are arranged in a circle. The entrance face of the bundle 18 is situated opposite the exit face 10 of the X-ray image intensifier 8. Bundle 18 is rotatable about the axis 15 which extends perpendicularly to the exit face 10 and through the center thereof.

The image conductor bundle 18 reforms the perspective images (which successively appear on the exit face 10 and which are arranged in a circle) on the image recording means 11a. The re-formed perspective images are the same size as the originals and are arranged in a circle having a larger diameter. During this operation, the bundle 18 is rotated in synchronism with the activation of the radiation sources so that the distribution of the perspective images on the image recording means 11a corresponds to the distribution of the perspective images on the exit screen 10. This is achieved by means of the control device 16 described with reference to FIG. 1a.

The same is applicable to the image separating system which is shown in FIG. 2c and which consists of, for example, two oppositely situated, suitably bent image conductor beams 20 and 21. This image separating system enables the transmission of two separate perspective images which simultaneously appear on the exit screen 10 of X-ray image intensifier 8 to the image recording means 11a without reduction.

The image conductor bundles 18, 20 and 21, shaped as shown in FIGS. 2b and 2c, can be provided at their exit with an additional optical system, for example a fibre-optical system (not shown) which images the perspective images on to the image recording means at an increased scale. The clearness of the layer images derived from the perspective images is thus increased.

Between the image separating system (16, 18 or 20 and 21) and the detector 8 or the image recording means 11a, an optical coupling liquid 26 (FIG. 2c) may be provided for the coupling in and out of the radiation. The image recording means 11a formed by an X-ray film, moreover, can be pressed, for example by means of a spring, against the image separating system in order to obtain an intimate contact between the image recording means and the image separating system, possibly in synchronism with the activation of the X-ray tubes 3.

As appears from FIG. 3, the image separating system may alternatively consist of an electron-optical deflection unit 22 which converts the perspective images successively appearing on the exit face 10 of the X-ray image intensifier 8 into electron-optical images. The electron-optical images are deflected or separated and converted into optical images again. The optical images are imaged in separated form on the image recording means. The deflection unit 22 may be a unit which is separated from the X-ray image intensifier 8 and which is coupled thereto, for example, by way of a fiber-optical system. The deflection unit 22, however, may alternatively be accommodated inside the X-ray image intensifier 8.

The image recording means may consist of, for example, a fluorescent screen 11b having a high afterglow persistence. This high afterglow persistence is provided so that the perspective images, which are imaged thereon in rapid succession, can be superposed to form layer images in real time by means of a lens matrix 23. Lens matrix 23 is arranged behind the fluorescent screen 11b. The fluorescent screen 11b may also be the exit screen of the electron-optical deflection unit 22. A frosted glass plate 24 or an image intensifier tube, camera or the like can then be arbitrarily positioned within the superposition zone of the perspective images, so that different layer images of the body can be obtained.

Behind the fluorescent screen 11b, a television camera for recording the perspective images may also be arranged. The images may be stored, for example, on a video disc. The superposition of the perspective images or television images in order to form a layer image can then be performed in a storage tube. This reconstruction method is known as "Elektronische Tomosynthese", and is described by K. Dümmling in the magazine "Der Radiologe" (Volume 9 (1969), pages 37-40. The perspective images recorded by means of the television camera can also be digitized, and the superposition can be performed in a computer.

In order to obtain layer images of constant quality and size, the device according to the invention may also be constructed as disclosed in German Patent Application No P 30 37 621.7 so that it can be adjusted to a given layer within the body. Relative movement between the device and the body produces images of other body layers.

What is claimed is:

1. A device for producing an image of a layer of a body, said device comprising:
   a single radiation detector situated on one side of the body;
   radiation source means on a side of the body opposite to the detector, said radiation source means arranged to sequentially irradiate the body from a plurality of radiation source positions in a single plane to form a sequence of perspective images of the body on the detector, at least two of the perspective images being at least partially spatially superposed on the detector;
   image recording means arranged to record the perspective images formed on the detector;
   image separating means arranged between the image recording means and the detector, said image separating means separating the perspective images so that no two perspective images are superposed on the image recording means; and
   means for superposing the recorded perspective images so as to construct an image of a layer of the body.

2. A device as claimed in claim 1, characterized in that the image separating means comprises an electron-optical deflection unit.

3. A device as claimed in claim 2, characterized in that the image recording means comprises a fluorescent screen.

4. A device as claimed in claim 3, characterized in that the fluorescent screen is an exit screen of the electron-optical deflection unit.

5. A device as claimed in claim 1, characterized in that the image separating means is an optical system for separating visible images.

6. A device as claimed in claim 5, characterized in that:
   the optical system comprises means for reducing the sizes of the perspective images; and
   the optical system is sequentially aimed at the perspective images formed on the detector.

7. A device as claimed in claim 5, characterized in that:
- the radiation source positions are situated on a circle; and
- the optical system comprises a bundle of image conductors arranged to be rotatable about an axis perpendicular to and passing through the center of the radiation detector, said bundle having an entrance face arranged opposite to the detector at a first distance from the axis and an exit face arranged opposite to the image recording means at a second distance from the axis greater than the first distance.

8. A device as claimed in claim 7, characterized in that the device comprises an enlargement optical system arranged at the exit face of the bundle of image conductors.

9. A device as claimed in claim 8, characterized in that the device comprises a plurality of optical image separating systems, the number of systems being less than or equal to the number of perspective images which can be simultaneously formed on the detector without being spatially superposed.

10. A device as claimed in claim 9, characterized in that the device further comprises optical coupling liquid between the detector and the optical system and between the image recording means and the optical system.

11. A device as claimed in claim 10, characterized in that the image recording means is a photosensitive film.

12. A device as claimed in claim 10, characterized in that:
- the image recording means comprises a fluorescent screen; and
- the means for superposing the perspective images comprises a lens matrix arranged behind the fluorescent screen.

13. A device as claimed in claim 12, characterized in that the fluorescent screen is an exit screen of an electron-optical deflection unit.

14. A device as claimed in claim 12, characterized in that the means for superposing the perspective images comprises a television camera and electronic means for storing and superposing the perspective images.

15. A device as claimed in claim 14, characterized in that the detector is an X-ray image intensifier.

* * * * *